United States Patent [19]

Sugimoto et al.

[11] Patent Number: 4,551,420
[45] Date of Patent: Nov. 5, 1985

[54] SILVER HALIDE PHOTOGRAPHIC LIGHT-SENSITIVE MATERIAL

[75] Inventors: Naohiko Sugimoto; Tetsuro Kojima, both of Kanagawa, Japan

[73] Assignee: Fuji Photo Film Co., Ltd., Kanagawa, Japan

[21] Appl. No.: 698,251

[22] Filed: Feb. 1, 1985

Related U.S. Application Data

[63] Continuation of Ser. No. 541,183, Oct. 12, 1983, abandoned.

[30] Foreign Application Priority Data

Oct. 12, 1982 [JP] Japan .................................. 57-178788

[51] Int. Cl.$^4$ ................................................. G03C 1/78
[52] U.S. Cl. .................................... 430/505; 430/512; 430/527; 430/931
[58] Field of Search ................. 430/512, 527, 931, 505

[56] References Cited

U.S. PATENT DOCUMENTS

| | | | |
|---|---|---|---|
| 4,045,229 | 8/1977 | Weber et al. | 430/512 |
| 4,195,999 | 4/1978 | Adachi et al. | 430/512 |
| 4,200,464 | 4/1980 | Shishido et al. | 430/512 |
| 4,307,184 | 12/1981 | Beretta et al. | 430/512 |
| 4,431,726 | 2/1984 | Kojima et al. | 430/512 |
| 4,443,534 | 4/1984 | Kojima et al. | 430/512 |

Primary Examiner—Jack P. Brammer
Attorney, Agent, or Firm—Sughrue, Mion, Zinn, Macpeak, and Seas

[57] ABSTRACT

A silver halide photographic light-sensitive material is disclosed which is comprised of a support base having thereon a light-sensitive silver halide emulsion layer and a light-insensitive layer. The material also includes an ultraviolet ray absorbing polymer latex and a fine grained silver halide having a diameter of 0.2 microns or less. The ultraviolet ray absorbing polymer latex is a polymer or copolymer having a repeating unit derived from a monomer represented by the general formula (I):

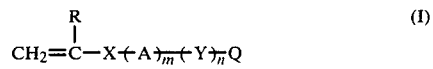

the substituents are defined within the specification. By utilizing the polymer latex of general formula (I) the occurance of static marks is almost completely prevented without causing undesirable effects on other film properties.

28 Claims, No Drawings

SILVER HALIDE PHOTOGRAPHIC LIGHT-SENSITIVE MATERIAL

This is a continuation of application Ser. No. 541,183, filed Oct. 12, 1983, now abandoned.

FIELD OF THE INVENTION

The present invention relates to a silver halide photographic light-sensitive material (hereinafter referred to simply as "photographic light-sensitive material"), and particularly to a photographic light-sensitive material having an improved antistatic and antiadhesive properties.

BACKGROUND OF THE INVENTION

Since photographic light-sensitive materials are generally composed of an electrically insulating support and photographic layers, static charges are frequently accumulated when the photographic materials are subjected to friction or separation caused by contacting with the surface of the same or different materials during steps for production of the photographic light-sensitive materials or when using them for photographic purposes. These accumulated static charges cause many problems. The most serious problem is discharge of accumulated static charges prior to development processing, by which the light-sensitive emulsion layer is exposed to light to form dot spots or branched or feathery linear specks when development of the photographic films is carried out. This phenomenon is the so-called static mark, to which the commercial value of the photographic films significantly deteriorates, and is sometimes entirely lost. For example, in the case of medical or industrial X-ray films, it is easily understood that the static marks may result in a very dangerous judgement or misdiagnosis. This phenomenon is a very troublesome problem, because it only becomes clear after carrying out development. Further, these accumulated static charges are also the origin of secondary problems such as adhesion of dusts to the surface of films, uneven coating, etc.

As described above, such static charges are frequently accumulated when producing and using photographic light-sensitive materials. For example, in the step for production, they are generated by friction of the photographic film contacting a roller or by separation of the emulsion face from the base face during rolling or unrolling. Further, they are generated on X-ray films in an automatic camera by contacting with or separating from mechanical parts or fluorescent sensitizing paper, or they are generated by contact with or separation from rollers and bars made of rubber, metal, or plastics in a bonding machine or an automatic developing machine in the developing shop or in a camera when using color negative films or color reversal films. In addition, they are generated by contact with packing materials, etc.

Static marks on photographic light-sensitive materials occurring due to accumulation and discharge of static charges increase with increases in the sensitivity of the photographic light-sensitive materials and an increase of the processing speed. Particularly, static marks are easily generated because of high sensitization of the photographic light-sensitive materials and severe processing conditions such as high speed coating, high speed photographing, and high speed automatic processing.

In order to prevent static charges, it is suitable to add antistatic agents to the photographic light-sensitive materials. However, antistatic agents used conventionally in other fields cannot be used freely for photographic light-sensitive materials, because they are subjected to various specific restrictions due to the nature of the photographic light-sensitive materials. More specifically, the antistatic agents capable being used in the photographic light-sensitive materials must not only have excellent antistatic ability, but also must be free from an adverse influence upon photographic properties of the photographic light-sensitive materials, such as sensitivity, fog, granularity, sharpness, etc. Further, they must not have an adverse influence upon film strength of the photographic light-sensitive materials (namely, that the photographic light-sensitive materials are not easily injured by friction or scratching). In addition, they must not have an adverse influence upon adhesion resistance (namely, that the photographic light-sensitive materials do not easily adhere when the surfaces of them are brought into contact with each other or with surfaces of other materials), they must not accelerate deterioration of processing solutions for the photographic light-sensitive materials, and they must not deteriorate adhesive strength between layers composing the photographic light-sensitive materials, etc. Accordingly, applications of antistatic agents to photographic light-sensitive materials are subject to many restrictions.

One method for overcoming problems caused by static charges comprises increasing electric conductivity of the surface of the photographic light-sensitive materials so that static charges disappear within a short time, prior to sparks discharging from the accumulated charges.

Accordingly, processes for improving the electrically conductive property of the support or the surface of various coating layers in the photographic light-sensitive materials have been proposed hitherto, and utilization of various hygroscopic substances, water-soluble inorganic salts, certain kinds of surface active agents and polymers, etc., has been attempted. For example, it has been known to use polymers as described in U.S. Pat. Nos. 2,882,157, 2,972,535, 3,062,785, 3,262,807, 3,514,291, 3,615,531, 3,753,716, 3,938,999, etc., surface active agents as described in U.S. Pat. Nos. 2,982,651, 3,428,456, 3,457,076, 3,454,625, 3,552,972, 3,655,387, etc., and metal oxides and colloidal silica as described in U.S. Pat. Nos. 3,062,700, 3,245,833, 3,525,621, etc.

However, many of these substances exhibit great specificity, depending upon the kind of film support or the photographic composition, and there are cases that, although they produce a good result on certain specific film supports photographic emulsions or other photographic constituting elements, they are not only useless for improving antistatic property when using different film supports and photographic constituting elements, but also have an adverse influence upon photographic properties.

On the other hand, there are many cases wherein, although they have excellent antistatic effects, they can not be used because of having an adverse influence upon photographic properties such as sensitivity, fog, granularity, sharpness, etc. For example, it has been well known that polyethylene oxide compounds have antistatic effects, but they often have an adverse influence upon photographic properties, such as increasing fog, densitization, deterioration of granularity, etc. Particularly, in light-sensitive materials in which both sides of the base are coated with photographic emulsions, such as medical direct X-ray light-sensitive materials, it has been difficult to develop techniques for effectively providing an antistatic property without having an adverse influence upon photographic properties. Thus, the application of antistatic agents to the photographic light-sensitive materials is very difficult, and their use is often limited to a certain range.

Another method for overcoming the problems of photographic light-sensitive materials caused by static charges is that which comprises controlling the triboelectric series of the surface of the light-sensitive materials to reduce generation of static charges caused by friction or contact as described above.

For example, it has been attempted to utilize fluorine containing surface active agents, as described in British Pat. Nos. 1,330,356 and 1,524,631, U.S. Pat. Nos. 3,666,478 and 3,589,906, Japanese Patent Publication No. 26687/77 and Japanese Patent Application (OPI) Nos. 46733/74 and 32322/76, etc., for photographic light-sensitive materials for the above-described purpose.

However, photographic light-sensitive materials containing these fluorine containing surface active agents generally have an electrostatic property of charging in negative polarity. Accordingly, although it is possible to adapt the triboelectric series of the surface of the light-sensitive materials for each triboelectric series of rubber rollers, Delrin rollers and nylon rollers by suitably combining the fluorine containing surface active agents with coating aids having an electrostatic property of charging in positive polarity, problems still occur. That is, when such prior art fluorine containing surface active agents are used so as to adapt for rubber, branched static marks occur due to Delrin, of which triboelectric series is situated on the positive side comparing to the triboelectric series of rubber; and when they are used so as to adapt for Delrin, spot static marks occur due to the rubber, of which triboelectric series is situated on the negative side comparing to the triboelectric series of Delrin. In order to compensate for those problems, a method for reducing the surface resistivity using high molecular weight electrolytes together with the fluorine containing surface active agents is known. However, such a method brings about various evil effects, for example, an adverse influence upon adhesion resistance, an adverse influence upon photographic properties. Therefore, it is impossible that these compounds are incorporated into photographic light-sensitive materials to the extent of obtaining sufficient antistatic property.

Still another method for preventing the occurrence of static marks is a method in which ultraviolet ray absorbing agents are employed. It has been known that a distribution of spectral energy of discharge luminescence which causes static marks is in a range of 200 nm to 500 nm and, particularly, the intensity thereof is high in a range of 300 nm to 400 nm, and light energy in this range causes occurrence of static marks. Accordingly, attempts have been made to prevent the occurrence of static marks by shielding ultraviolet rays in a range of 300 to 400 nm by means of ultraviolet ray absorbing agents, as described in, for example, Japanese Patent Publication No. 10726/75, Japanese Patent Application (OPI) No. 26021/76, French Patent No. 2,036,679, etc.

However, it is very difficult to effectively shield ultraviolet rays in a range of 300 to 400 nm by means of conventional ultraviolet ray absorbing agents without an adverse influence upon photographic sensitivity and film property (adhesion resistance).

SUMMARY OF THE INVENTION

Therefore, an object of the present invention is to provide a photographic light-sensitive material in which the occurrence of static marks is almost prevented without degradation of film properties.

Other objects of the present invention will be apparent from the following detailed description and examples.

As a result of extensive investigations, it has now been found that these objects of the present invention can be attained by a silver halide photographic light-sensitive material comprising a support having thereon at least one light-sensitive silver halide emulsion layer and at least one light-insensitive layer, the photographic light-sensitive material containing (A) an ultraviolet ray absorbing polymer latex which is a polymer or a copolymer having a repeating unit derived from a monomer represented by the following general formula (I):

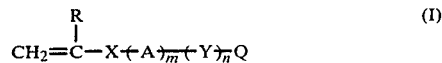

(I)

wherein R represents a hydrogen atom, a lower alkyl group having from 1 to 4 carbon atoms (for example, a methyl group, an ethyl group, a n-propyl group, an isopropyl group or a n-butyl group, etc.) or a chlorine atom; X represents —CONH—, —COO— or a phenylene group; A represents a linking group selected from an alkylene group having from 1 to 20 carbon atoms (for example, a methylene group, an ethylene group, a trimethylene group, a 2-hydroxytrimethylene group, a pentamethylene group, hexamethylene group, an ethylethylene group, a propylene group or a decamethylene group, etc.) or an arylene group having from 6 to 20 carbon atoms (for example, a phenylene group, etc.); Y represents —COO—, —OCO—, —CONH—, —NHCO—, —SO$_2$NH—, —NHSO$_2$—, —SO$_2$— or —O—; m represents 0 or an integer of 1; n represents 0 or an integer of 1; and Q represents an ultraviolet ray absorbing group represented by the following general formula (II) or (III)

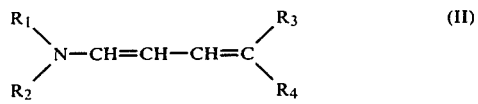

(II)

wherein R$_1$ and R$_2$, which may be the same or different, each represents a hydrogen atom, an alkyl group having from 1 to 20 carbon atoms (for example, a methyl group, an ethyl group, a n-butyl group, a n-hexyl group, a cyclohexyl group, a n-decyl group, a n-dodecyl group, a n-octadecyl group, an eicosyl group, a methoxyethyl group, an ethoxypropyl group, a 2-ethylhexyl group, a hydroxyethyl group, a chloropropyl group, an N,N-diethylaminopropyl group, a cyanoethyl group, a phenethyl group, a benzyl group, a p-tert-butylphenethyl group, a p-tert-octylphenoxyethyl group, a 3-(2,4-di-tert-amylphenoxy)propyl group, an ethoxycarbonylmethyl group, a 2-(2-hydroxyethoxy)ethyl group, a 2-furylethyl group, etc.) or an aryl group having from 6 to 20 carbon atoms (for example, a tolyl group, a phenyl group, an anisyl group, a mesityl group, a chlorophenyl group, a 2,4-di-tert-amylphenyl group, a naphthyl group, etc.) provided that the both of $R_1$ and $R_2$ do not simultaneously represent hydrogen atoms, and further $R_1$ and $R_2$ may combine to form an atomic group necessary to form a cyclic amino group (for example, a piperidino group, a morpholino group, a pyrrolidino group, a hexahydroazepino group, a piperazino group, etc.); $R_3$ represents a cyano group, —$COOR_5$, —$CONHR_5$, —$COR_5$ or —$SO_2R_5$; and $R_4$ represents a cyano group, —$COOR_6$, —$CONHR_6$, —$COR_6$ or —$SO_2R_6$, wherein $R_5$ and $R_6$ each represents an alkyl group having from 1 to 20 carbon atoms or an aryl group having from 6 to 20 carbon atoms, each having the same meanings as those for $R_1$ and $R_2$, and further $R_5$ and $R_6$ may combine to form an atomic group necessary to form a 1,3-dioxocyclohexane ring (for example, a dimedone ring, a 1,3-dioxo-5,5-diethylcyclohexane ring, etc.), a 1,3-diaza-2,4,6-trioxocyclohexane ring (for example, a barbituric acid ring, a 1,3-dimethylbarbituric acid ring, a 1-phenylbarbituric acid ring, a 1-methyl-3-octylbarbituric acid ring, a 1-ethyl-3-octylbarbituric acid ring, a 1-ethyl-3-octyloxycarbonylethylbarbituric acid ring, etc.), a 1,2-diaza-3,5-dioxocyclopentane ring (for example, a 1,2-diaza-1,2-dimethyl-3,5-dioxocyclopentane ring, a 1,2-diaza-1,2-diphenyl-3,5-dioxocyclopentane ring, etc.) or a 2,4-diaza-1-alkoxy-3,5-dioxocyclohexene ring (for example, a 2,4-diaza-1-ethoxy-4-ethyl-3,5-dioxocyclohexene ring, a 2,4-diaza-1-ethoxy-4-[3-(2,4-di-tert-amylphenoxy)-propyl]-3,5-dioxocyclohexene ring, etc.); and at least one of $R_1$, $R_2$, $R_3$ and $R_4$ bonds to the vinyl group through the above-described linking group,

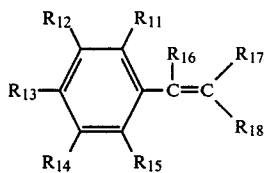

wherein $R_{11}$, $R_{12}$, $R_{13}$, $R_{14}$ and $R_{15}$ each represents a hydrogen atom, a halogen atom (for example, a chlorine atom or a bromine atom), an alkyl group having from 1 to 20 carbon atoms (for example, a methyl group, an ethyl group, a n-propyl group, an isopropyl group, a n-butyl group, a tert-butyl group, a n-amyl group, a tert-amyl group, a n-octyl group, a tert-octyl group, a methoxyethyl group, an ethoxypropyl group, a hydroxyethyl group, a chloropropyl group, a benzyl group or a cyanoethyl group, etc.), an aryl group having from 6 to 20 carbon atoms (for example, a phenyl group, a tolyl group, a mesityl group, a chlorophenyl group, etc.), an alkoxy group having from 1 to 20 carbon atoms (for example, a methoxy group, an ethoxy group, a propoxy group, a butoxy group, an octyloxy group, a 2-ethylhexyloxy group, a methoxymethoxy group, a methoxyethoxy group or an ethoxyethoxy group, etc.), an aryloxy group having from 6 to 20 carbon atoms (for example, a phenoxy group or a 4-methylphenoxy group, etc.), an alkylthio group having from 1 to 20 carbon atoms (for example, a methylthio group, an ethylthio group, a propylthio group or a n-octylthio group, etc.), an arylthio group having from 6 to 20 carbon atoms (for example, a phenylthio group, etc.), an amino group, an alkylamino group having from 1 to 20 carbon atoms (for example, a methylamino group, an ethylamino group, a benzylamino group, a dimethylamino group or a diethylamino group, etc.), an arylamino group having from 6 to 20 carbon atoms (for example, an anilino group, a diphenyl amino group, an anisidino group or a toluidino group, etc.), a hydroxy group, a cyano group, a nitro group, an acylamino group (for example, an acetylamino group, etc.), a carbamoyl group (for example, a methylcarbamoyl group or a dimethylcarbamoyl group, etc.), a sulfonyl group (for example, a methylsulfonyl group or a phenylsulfonyl group, etc.), a sulfamoyl group (for example, an ethylsulfamoyl group or a dimethylsulfamoyl group, etc.), a sulfonamido group (for example, a methanesulfonamido group, etc.), an acyloxy group (for example, an acetoxy group or a benzoyloxy group, etc.) or an oxycarbonyl group (for example, a methoxycarbonyl group, an ethoxycarbonyl group or a phenoxycarbonyl group, etc.), and $R_{11}$ and $R_{12}$, $R_{12}$ and $R_{13}$, $R_{13}$ and $R_{14}$ or $R_{14}$ and $R_{15}$ may form a 5- or 6-membered ring by ring closure (for example, a methylenedioxy group, etc.). $R_{16}$ represents a hydrogen atom, or an alkyl group having from 1 to 20 carbon atoms (for example, a methyl group, an ethyl group, a n-propyl group, an isopropyl group, a n-butyl group, a n-amyl group or a n-octyl group, etc.), $R_{17}$ represents a cyano group, —$COOR_{19}$, —$CONHR_{19}$, —$COR_{19}$ or —$SO_2R_{19}$, and $R_{18}$ represents a cyano group, —$COOR_{20}$, —$CONHR_{20}$, —$COR_{20}$ or —$SO_2R_{20}$, wherein $R_{19}$ and $R_{20}$ each represents the same alkyl group or aryl group as described above; and at least one of $R_{11}$, $R_{12}$, $R_{13}$, $R_{14}$, $R_{15}$, $R_{16}$, $R_{17}$ and $R_{18}$ bonds to the vinyl group through the above-described linking group, and (B) a fine grained silver halide having a diameter of 0.2 microns or less.

DETAILED DESCRIPTION OF THE INVENTION

Of the ultraviolet ray absorbing groups represented by the general formula (II), those wherein $R_1$ and $R_2$ each represents an alkyl group having from 1 to 20 carbon atoms, $R_3$ represents a cyano group or —$SO_2R_5$, $R_4$ represents a cyano group or —$COOR_6$, and $R_5$ and $R_6$ each represents an alkyl group having from 1 to 20 carbon atoms or an aryl group having from 6 to 20 carbon atoms are preferred.

Of the ultraviolet ray absorbing groups represented by the general formula (II), those wherein $R_1$ and $R_2$ each represents an alkyl group having from 1 to 6 carbon atoms, $R_3$ represents —$SO_2R_5$, $R_4$ represents —$COOR_6$, $R_5$ represents a phenyl group which may be substituted (for example, a phenyl group, a tolyl group, etc.), and $R_6$ represents an alkyl group having from 1 to 20 carbon atoms are particularly preferred.

Of the ultraviolet ray absorbing groups represented by the general formula (III), those wherein $R_{11}$, $R_{12}$, $R_{13}$, $R_{14}$ and $R_{15}$ each represents a hydrogen atom, a halogen atom, an alkyl group having from 1 to 20 carbon atoms, an aryl group having from 6 to 20 carbon atoms, an alkoxy group having from 1 to 20 carbon atoms, an aryloxy group having from 6 to 20 carbon atoms, an alkylamino group having from 1 to 20 carbon atoms, an arylamino group having from 6 to 20 carbon atoms, a hydroxy group, an acylamino group, a carbamoyl group, an acyloxy group or an oxycarbonyl group, and $R_{11}$ and $R_{12}$, $R_{12}$ and $R_{13}$, $R_{13}$ and $R_{14}$ or $R_{14}$ and $R_{15}$ may form a ring, $R_{16}$ represents a hydrogen atom, or an alkyl group having from 1 to 20 carbon atom, $R_{17}$ represents a cyano group, —$COOR_{19}$—, —$CONHR_{19}$—, —$COR_{19}$ or —$SO_2R_{19}$, and $R_{18}$ represents a cyano group, —$COOR_{20}$, —$CONHR_{20}$, —$COR_{20}$ or —$SO_2R_{20}$, wherein $R_{19}$ and $R_{20}$ each represents an alkyl group having from 1 to 20 carbon atoms or an aryl group having from 6 to 20 carbon atoms, and at least one of $R_{11}$, $R_{12}$, $R_{13}$, $R_{14}$, $R_{15}$, $R_{16}$, $R_{17}$ and $R_{18}$ bonds to the vinyl group through the above described linking group are preferred.

In compounds represented by the above described general formula (I), it is particularly preferred that R represents a hydrogen atom, a lower alkyl group having from 1 to 4 carbon atoms or a chlorine atom, X represents —COO—, m and n each represents 0, and Q represents an ultraviolet ray absorbing group represented by the general formula (III) wherein $R_{11}$, $R_{12}$, $R_{14}$ and $R_{15}$ each represents a hydrogen atom, $R_{13}$ represents a hydrogen atom or an alkyl group having from 1 to 5 carbon atoms, $R_{16}$ represents a hydrogen atom, $R_{17}$ represents a cyano group, and $R_{18}$ represents —$COOR_{20}$ wherein $R_{20}$ represents an alkylene group having from 1 to 20 carbon atoms which bonds to the vinyl group.

Examples of monomers (comonomers) used for copolymerizing with the ultraviolet ray absorbing monomers, include an ethylenically unsaturated monomer such as an ester, preferably a lower alkyl ester, and an amide, derived from an acrylic acid, for example, acrylic acid, α-chloroacrylic acid, an α-alkylacrylic acid such as methacrylic acid, etc. (for example, acrylamide, methacrylamide, tert-butylacrylamide, methyl acrylate, methyl methacrylate, ethyl acrylate, ethyl methacrylate, n-propyl acrylate, n-butyl acrylate, 2-ethylhexyl acrylate, n-hexyl acrylate, octyl methacrylate, lauryl methacrylate and methylenebisacrylamide, etc.), a vinyl ester (for example, vinyl acetate, vinyl propionate and vinyl laurate, etc.), acrylonitrile, methacrylonitrile, an aromatic vinyl compound (for example, styrene and a derivative thereof such as vinyl toluene, divinylbenzene, vinylacetophenone, sulfostyrene and styrenesulfinic acid, etc.), itaconic acid, citraconic acid, crotonic acid, vinylidene chloride, a vinyl alkyl ether (for example, vinyl ethyl ether, etc.), a maleic acid ester, N-vinyl-2-pyrrolidone, N-vinylpyridine and 2- and 4-vinylpyridine, etc.

Of these monomers, an acrylic acid ester, a methacrylic acid ester and an aromatic vinyl compound are particularly preferred.

Two or more of the above described comonomer compounds may be used together. For example, it is possible to use n-butyl acrylate and divinylbenzene, styrene and methyl methacrylate, or methyl acrylate and methacrylic acid.

The ethylenically unsaturated monomer which is used to copolymerize with the ultraviolet ray absorbing monomer corresponding to the above described general formula (I) can be selected so as to have a good influence upon physical properties and/or chemical properties of the copolymer to be prepared, for example, solubility, compatibility with a binder such as gelatin in the photographic colloid composition or other photographic additives, for example, known photographic ultraviolet ray absorbing agents, known photographic antioxidants and known color image forming agents, flexibility and thermal stability thereof, etc.

For example, in case of hardening a latex itself in order to harden the hydrophilic colloid layer, it is preferred to use a comonomer having a high glass transition point (Tg) (for example, styrene or methyl methacrylate).

The ultraviolet ray absorbing polymer latex used in the present invention may be prepared by an emulsion polymerization process or may be prepared by adding a solution prepared by dissolving an oleophilic polymer obtained by polymerization of an ultraviolet ray absorbing monomer in an organic solvent (for example, ethyl acetate) to an aqueous solution of gelatine together with a surface active agent and stirring to disperse in the form of a latex.

These processes can be applied to preparation of homopolymers and preparation of copolymers. In the latter case, it is preferred that a comonomer is liquid, because it functions as a solvent for the ultraviolet ray absorbing monomer which is solid in a normal state when carrying out emulsion polymerization.

Free radical polymerization of an ethylenically unsaturated solid monomer is initiated with the addition of a free radical which is formed by thermal decomposition of a chemical initiator, an action of a reducing agent to an oxidizing compound (a redox initiator) or a physical action such as irradiation of ultraviolet rays or other high energy radiations, high frequencies, etc.

Examples of principal chemical initiators include a persulfate (for example, ammonium persulfate or potassium persulfate, etc.), hydrogen peroxide, a peroxide (for example, benzoyl peroxide or chlorobenzoyl peroxide, etc.) and an azonitrile compound (for example, 4,4'-azobis(4-cyanovaleric acid) or azobisisobutyronitrile, etc.), etc.

Examples of conventional redox initiators include hydrogen peroxide-iron (II) salt, potassium persulfate-potassium bisulfate and cerium salt-alcohol, etc.

Examples of the initiators and the functions thereof have been described in F. A. Bovey, *Emulsion Polymerization*, issued by Interscience Publishes Inc. New York, 1955, pages 59–93.

As an emulsifier which can be used in the emulsion polymerization, a compound having surface activity is used. Preferably examples of them include a sulfonate a sulfate, a cationic compound, an amphoteric compound and a high molecular weight protective colloid. Specific examples of the emulsifiers and the functions thereof are described in *Belgische Chemische Industrie*, vol. 28, pages 16–20 (1963).

On the other hand, when dispersing the oleophilic polymer ultraviolet ray absorbing agent in an aqueous solution of gelatin in the form of a latex, an organic solvent used for dissolving the oleophilic polymer ultraviolet ray absorbing agent is removed from the mixture prior to coating of the dispersion or by volatilization during drying of the dispersion coated, although the latter is less preferable.

Useful solvents include those which have a certain degree of water solubility such that they are capable of being removed by washing with water in a gelatin noodle state and those which can be removed by spray drying, vacuum or steam purging.

Further, examples of the organic solvents capable of being removed include an ester (for example, a lower alkyl ester), a lower alkyl ether, a ketone, a halogenated hydrocarbon (for example, methylene chloride, trichloroethylene, etc.), a fluorinated hydrocarbon, an alcohol (for example, an alcohol from n-butyl alcohol to octyl alcohol and a combination thereof.

Any type of dispersing agent can be used in the dispersion of the oleophilic polymer ultraviolet ray absorbing agent. However, ionic surface active agents and particularly anionic surface active agents are preferred.

Further, it is possible to use ampholytic agents such as C-cetylbetaine, N-alkylaminopropionic acid salts or N-alkyliminodipropionic acid salts.

In order to increase the dispersion stability and to improve the flexibility of the emulsion coated, a small amount (not more than 50% by weight of the ultraviolet ray absorbing polymer) of a permanent solvent, namely, a water immiscible organic solvent having a high boiling point (i.e., above 200° C.) may be added. It is necessary for the concentration of the permanent solvent to be sufficiently low in order to plasticize the polymer while it is kept in a state of a solid particle. Furthermore, when using the permanent solvent, it is preferred that the amount thereof is as small as possible so as to decrease the thickness of the final emulsion layer or the hydrophilic colloid layer in order to maintain good sharpness.

It is preferred that the amount of the ultraviolet ray absorbing agent portion (monomer represented by the general formula (I)) in the ultraviolet ray absorbing polymer latex according to the present invention is generally from 5% to 100% by weight, and an amount of from 50% to 100% by weight is particularly preferred from the viewpoint of the thickness of the layer and stability.

In the following, typical examples of the ultraviolet ray absorbing monomers corresponding to the general formula (I) according to the present invention are described, but the present invention is not to be construed as being limited thereto.

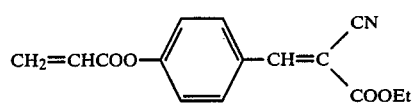 (1)

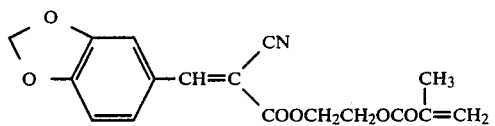 (2)

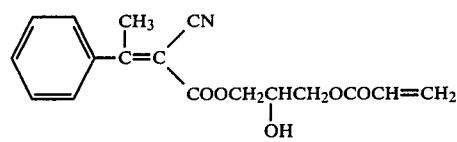 (3)

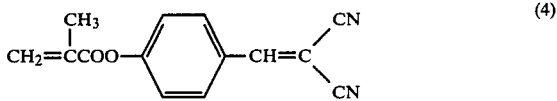 (4)

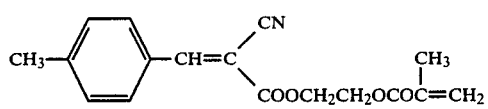 (5)

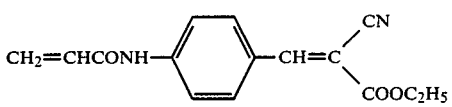 (6)

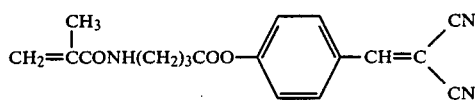 (7)

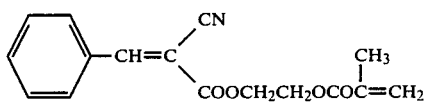 (8)

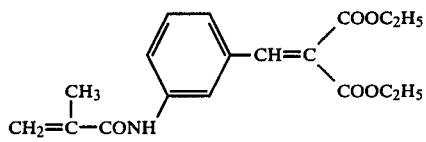 (9)

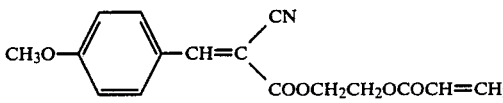 (10)

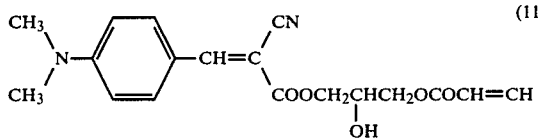 (11)

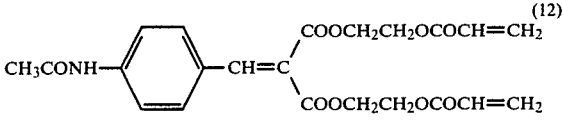 (12)

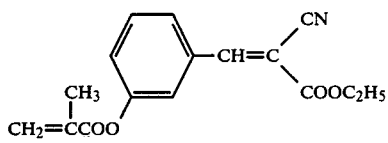 (13)

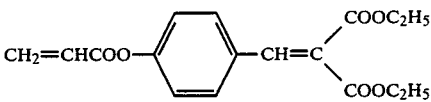 (14)

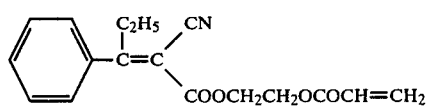 (15)

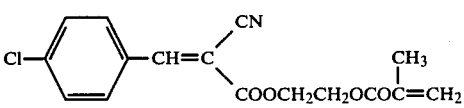 (16)

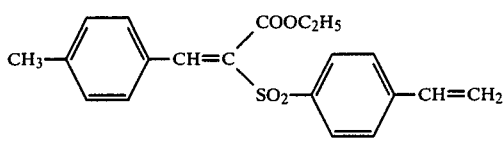 (17)

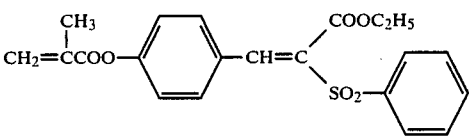 (18)

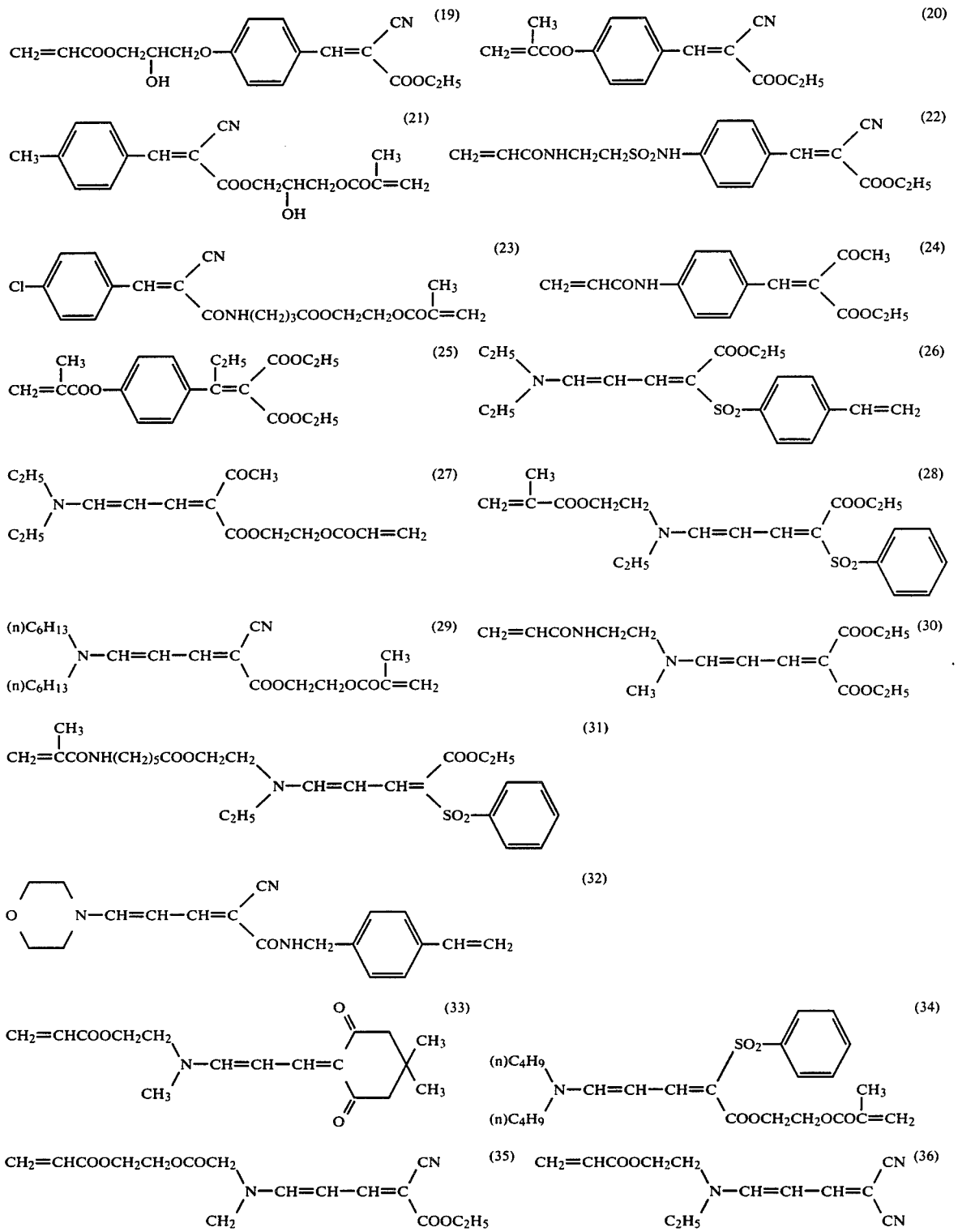
Specific examples of preferred compositions of the homopolymer or copolymer ultraviolet ray absorbing agents used in the present invention are described below, but the present invention is not to be construed as being limited thereto.
P-1 to P-36: Homopolymers of the above Compounds (1) to (36)
P-37: Copolymer of Compound (5): methyl methacrylate = 7:3

P-38: Copolymer of Compound (5): methyl methacrylate=5:5
P-39: Copolymer of Compound (5): methyl acrylate=7:3
P-40: Copolymer of Compound (8): styrene=5:5
P-41: Copolymer of Compound (8): butyl acrylate=7.5:2.5
P-42: Copolymer of Compound (1): methyl methacrylate=7:3
P-43: Copolymer of Compound (1): methyl methacrylate=5:5
P-44: Copolymer of Compound (8): methyl acrylate=7:3
P-45: Copolymer of Compound (2): methyl methacrylate=5:5
P-46: Copolymer of Compound (16): methyl methacrylate=7:3
P-47: Copolymer of Compound (16): methyl acrylate=5:5
P-48: Copolymer of Compound (26): methyl methacrylate=8:2
P-49: Copolymer of Compound (26): methyl methacrylate=5:5
P-50: Copolymer of Compound (36): n-butyl acrylate=7:3
P-51: Copolymer of Compound (28): methyl methacrylate=7:3
P-52: Copolymer of Compound (31): methyl methacrylate=8:2
P-53: Copolymer of Compound (36): n-butyl acrylate=5:5

The ultraviolet ray absorbing monomers corresponding to the general formula (I) can be synthesized by reacting a compound synthesized by the process described, for example, in U.S. Pat. Nos. 4,200,464 and 4,195,999, Beilsteins Handbuch der Organischen Chemie (4th eddition) vol. 10, page 521 (1942), Japanese Patent Application (OPI) No. 56620/76, etc. with an acid halide of acrylic acid or α-substituted acrylic acid such as acryloyl chloride or methacryloyl chloride, and can be synthesized by a reaction of 2-cyano-3-phenylacrylic acid with hydroxyethyl acrylate, hydroxyethyl methacrylate or glycidyl acrylate, etc. as described, for example, in Japanese Patent Application (OPI) Nos. 28122/74 and 11102/73, etc.

Typical examples of syntheses of the compounds used in the present invention are set forth below.

[A] Syntheses of Monomer Compounds

SYNTHESIS EXAMPLE 1

Synthesis of Compound (5)

Tolualdehyde (400 g), cyanoacetic acid (311 g), acetic acid (60 ml) and ammonium acetate (25.6 g) were refluxed in ethyl alcohol (1.6 l) for 4 hours with heating. After the reaction, the mixture was concentrated to 600 ml by removing ethyl alcohol under a reduced pressure, followed by pouring into 1 liter of ice water to separate crystals. The separated crystals were collected by suction filtration and recrystallized from 2 liters of ethyl alcohol to obtain 560 g of 2-cyano-3-(4-methylphenyl)acrylic acid which melted at 210° to 215° C. The resulting compound (320 g) and thionyl chloride (252 g) were dissolved in acetonitrile (200 ml) with heating for 1 hour. After the reaction, the acetonitrile and the thionyl chloride were distilled off under a reduced pressure, and the resulting solid was added to a solution consisting of hydroxyethyl methacrylate (244.8 g), pyridine (149 g) and acetonitrile (2 l). The reaction was carried out for 2 hours while keeping the reaction temperature below 40° C. After the reaction, the reaction solution was poured into ice water to separate crystals, and the resulting crystals were recrystallized from ethyl alcohol (3 l) to obtain 360 g of the desired compound which melted at 74° to 75° C.

The desired compound was confirmed by the results of IR, NMR and elemental analysis.

Elemental Analysis for $C_{17}H_{17}NO_4$: Calculated: H: 5.72%, C: 68.22%, N: 4.68%. Found: H: 5.75%, C: 68.16%, N: 4.76%.

$\lambda_{max}^{CH_3OH} = 311$ nm.

SYNTHESIS EXAMPLE 2

Synthesis of Compound (8)

Benzaldehyde (200 g), cyanoacetic acid (176 g), acetic acid (30 ml) and ammonium acetate (14.5 g) were refluxed for 4 hours in ethyl alcohol (800 ml) with heating. After the reaction, the mixture was concentrated to 400 ml by removing ethyl alcohol under a reduced pressure, followed by pouring into 1 liter of ice water to separate crystals. The resulting crystals were recrystallized from 250 ml of acetonitrile to obtain 265 g of 2-cyano-3-phenylacrylic acid which melted at 184° to 188° C. The resulting compound (150 g) and thionyl chloride (176 g) were dissolved in acetonitrile (100 ml) with heating for 1 hour. After the reaction, the acetonitrile and the thionyl chloride were distilled off under a reduced pressure, and the resulting solid was added to a solution consisting of hydroxyethyl methacrylate (124 g), pyridine (75 g) and acetonitrile (1 l). The reaction was carried out for 2 hours while keeping the reaction temperature below 40° C. After the reaction, the reaction solution was poured into ice water to separate crystals, and the resulting crystals were recrystallized form ethyl alcohol (1 l) to obtain 205 g of the desired compound which melted at 68° to 70° C.

The desired compound was confirmed by the results of IR, NMR and elemental analysis.

Elemental Analysis for $C_{16}H_{14}NO_4$: Calculated: H: 4.96%, C: 67.60%, N: 4.93%. Found: H: 4.87%, C: 67.65%, N: 4.99%.

$\lambda_{max}^{CH_3OH} = 298$ nm.

SYNTHESIS EXAMPLE 3

Synthesis of Compound (1)

4-hydroxybenzaldehyde (30 g), ethyl cyanoacetate (31.7 g), acetic acid (4.5 ml) and ammonium acetate (1.9 g) were refluxed in ethyl alcohol (100 ml) for 4 hours with heating. After the reaction, the reaction solution was poured into 500 ml of ice water to separate crystals. The resulting crystals were recrystallized from methyl alcohol (400 ml) to obtain 65 g of ethyl 2-cyano-3-(4-hydroxyphenyl)acrylate which melted at 89° to 91° C. The resulting compound (10.9 g) and pyridine (4.3 g) were dissolved in tetrahydrofuran (100 ml), and acryloyl chloride (4.5 g) was added dropwise thereto. The reaction was carried out for 2 hours while keeping the reaction temperature below 40° C. After the reaction, the reaction solution was poured into ice water to separate crystals, and the resulting crystals were recrystallized from methyl alcohol (100 ml) to obtain 11 g of the desired compound which melted at 82° to 85° C. The desired compound was confirmed by the results of IR, NMR and elemental analysis.

Elemental Analysis for C$_{15}$H$_{13}$NO$_4$: Calculated: H: 4.83%, C: 66.41%, N: 5.16%. Found: H: 4.91%, C: 66.42%, N: 5.08%.

$\lambda_{max}^{CH3OH} = 323$ nm.

SYNTHESIS EXAMPLE 4

Synthesis of Compound (26)

3-Anilinoacroleinanil (45 g) are ethyl(4-vinylphenyl)-sulfonyl acetate (51 g) were heated at 85° to 90° C. for 2 hours in acetic anhydride (50 ml) under nitrogen atmosphere. After removing the acetic anhydride under a reduced pressure, ethyl alcohol (250 ml) and diethylamine (73 g) were added to the residue and the mixture was refluxed for 2 hours. The reaction solution was poured into ice water and the light yellow precipitates thus-formed were separated and recrystallized from ethyl alcohol (300 ml) to obtain 58 g of the desired compound which melted at 117° to 118° C.

$\lambda_{max}^{CH3COOC2H5} = 372$ nm

The desired compound was confirmed by the results of IR, NMR and elemental analysis.

Elemental Analysis for C$_{19}$H$_{25}$NO$_4$S: Calculated: H: 6.93%, C: 62.78%, N: 3.85%. Found: H: 6.88%, C: 62.87%, N: 3.80%.

SYNTHESIS EXAMPLE 5

Synthesis of Compound (28)

3-Anilinoacroleinanil (29 g) and ethylphenylsulfonyl acetate (30 g) were heated at 85° to 90° C. for 2 hours in acetic anhydride (30 ml). Then, the acetic anhydride was removed under a reduced pressure, to the residue were added ethyl alcohol (200 ml) and ethyl hydroxyethylamine (12 g) and the mixture was refluxed for 2 hours. The reaction solution was poured into ice water and the light yellow precipitates thus-formed were separated and recrystallized from ethyl acetate to obtain 36 g of ethyl 5-(N-ethyl-N-hydroxyethylamino)-2-phenylsulfonyl-2,4-pentadienoate which melted at 107° C.

The resulting compound (30 g) and pyridine (7 ml) were dissolved in acetonitrile (100 ml) and to the solution was added dropwise methacryloyl chloride (16 g). The mixture was reacted for 2 hours while maintaining the reaction temperature below 40° C. Then, the acetonitrile was distilled off, and the residue was passed through a chromatographic column with Kieselgel 60 (manufactured by Merk Co.) and the n-hexane-ethyl acetate effluent was collected. The solvent was distilled off and 25 g of the desired oily compound was obtained.

$\lambda_{max}^{CH3COOC2H5} = 372$ nm.

The desired compound was confirmed by the results of IR, NMR and elemental analysis.

Elemental Analysis for C$_{21}$H$_{27}$NO$_6$S: Calculated: H: 6.46%, C: 59.84%, N: 3.32%. Found: H: 6.54%, C: 59.71%, N: 3.35%.

[B] Synthesis of Polymer Compounds

SYNTHESIS EXAMPLE 6

Synthesis of Homopolymer latex of Compound (5)

600 ml of an aqueous solution containing 10 g of a sodium salt of oleylmethyltauride was heated to 90° C. while slowly passing a nitrogen stream therethrough under stirring. To the resulting mixture, 20 ml of an aqueous solution containing 350 mg of potassium persulfate was added. Then, a solution prepared by dissolving 50 g of ultraviolet ray absorbing monomer (5) in 200 ml of ethanol by heating was added thereto. After addition, the mixture was stirred for 1 hour while heating to 85° to 90° C., and 10 ml of an aqueous solution containing 150 mg of potassium persulfate was added thereto. After the reaction was further carried out for 1 hour, the ethanol was distilled off as an azeotropic mixture with water. The latex thus-formed was cooled. After the pH was adjusted to 6.0 with a 1N sodium hydroxide solution, the latex was filtered. The concentration of the polymer in the latex was 7.81%. Further, the latex had the absorption maximum at 330 nm in the aqueous system.

SYNTHESIS EXAMPLE 7

Synthesis of Copolymer latex of Compound (8) and n-butyl acrylate 800 ml of an aqueous solution containing 15 g of sodium salt of oleylmethyltauride was heated to 90° C. while slowly passing a nitrogen stream therethrough under stirring. To the resulting mixture, 20 ml of an aqueous solution containing 525 mg of potassium persulfate was added. Then, 50 g of ultraviolet ray absorbing monomer (8) and 25 g of n-butyl acrylate were dissolved in 200 ml of ethanol with heating, and the resulting solution was added to the above mixture. After addition, the mixture was stirred for 1 hour with heating to 85° to 90° C., and 10 ml of an aqueous solution containing 225 mg of potassium persulfate was added thereto. After the reaction was further carried out for 1 hour, the ethanol and the n-butyl acrylate not reacted were distilled off as an azeotropic mixture with water. The latex thus-formed was cooled. After the pH was adjusted to 6.0 with a 1N sodium hydroxide solution, the latex was filtered. The concentration of the copolymer in the latex was 10.23%. As a result of nitrogen analysis it was found that the copolymer synthesized contained 65.8% of the ultraviolet ray absorbing monomer unit. Further, the latex had the absorption maximum at 316 nm in the aqueous system.

SYNTHESIS EXAMPLE 8

Synthesis of Copolymer latex of Compound (5) and methyl methacrylate 4 l of an aqueous solution containing 75 g of sodium salt of oleylmethyltauride was heated to 90° C. while slowly passing a nitrogen stream therethrough under stirring. To the resulting mixture, 50 ml of an aqueous solution containing 2.6 g of potassium persulfate was added. Then, 300 g of ultraviolet ray absorbing monomer (5) and 60 g of methyl methacrylate were dissolved in 1 l of ethanol, and the resulting solution was added to the above mixture. After addition, the mixture was stirred for 1 hour while heating to 85° to 90° C., and 20 ml of an aqueous solution containing 1.1 g of potassium persulfate was added thereto. After the reaction was further carried out for 1 hour, the ethanol and the methyl methacrylate not reacted were distilled off as an azeotropic mixture with water. The latex thus-formed was cooled. After the pH was adjusted to 6.0 with a 1N sodium hydroxide solution, the latex was filtered. The concentration of the copolymer in the latex was 9.42%. As a result of nitrogen analysis it was found that the copolymer synthesized contained 78.9% of the ultraviolet ray absorbing monomer unit. Further, the latex had the absorption maximum at 327 nm in the aqueous system.

SYNTHESIS EXAMPLE 9

Synthesis of Copolymer latex of Compound (1) and methyl methacrylate 1 l of an aqueous solution containing 15 g of sodium salt of oleylmethyltauride was heated to 90° C. while slowly passing a nitrogen stream therethrough under stirring. To the resulting mixture, 20 ml of an aqueous solution containing 225 mg of potassium persulfate was added. Then, 10 g of methyl methacrylate was added thereto, and the mixture was stirred for 1 hour while heating to 85° to 90° C. to synthesize a latex (a). Then, to the resulting latex (a), a solution prepared by dissolving 50 g of ultraviolet ray absorbing monomer (1) and 10 g of methyl methacrylate in 200 ml of ethanol was added and thereafter 20 ml of an aqueous solution containing 300 mg of potassium persulfate was added. After the reaction was further carried out for 1 hour, 20 ml of an aqueous solution containing 225 mg of potassium persulfate was added. After subsequently carrying out the reaction for 1 hour, the ethanol and the methyl methacrylate not reacted were distilled off as an azeotropic mixture with water. The latex thus-formed was cooled. After the pH was adjusted to 6.0 with a 1N sodium hydroxide solution, the latex was filtered. The concentration of the copolymer in the latex was 8.38% as a result of nitrogen analysis it was found that the copolymer synthesized contained 62.3% of the ultraviolet ray absorbing monomer unit.

SYNTHESIS EXAMPLE 10

Synthesis of oleophilic polymer ultraviolet ray absorbing agent (1)

21 g of ultraviolet ray absorbing monomer (8) and 9 g of methyl acrylate were dissolved in 150 ml of dioxane. While stirring the resulting solution by heating at 70° C. under a nitrogen stream, a solution prepared by dissolving 270 mg of 2,2'-azobis-(2,4-dimethylvaleronitrile) in 5 ml of dioxane was added, and the reaction was carried out for 5 hours. Then, the resulting product was poured into 2 l of ice water, and the solid thus-separated was collected by filtration and thoroughly washed with water. The product was dried to obtain 25.3 g of the oleophilic polymer ultraviolet ray absorbing agent. As a result of nitrogen analysis of the oleophilic polymer ultraviolet ray absorbing agent, it was found that the copolymer synthesized contained 64.5% of the ultraviolet ray absorbing monomer unit.

$\lambda_{max}^{CH3COOC2H5} = 300$ nm.

Process for preparing ultraviolet ray absorbing polymer latex (A)

Two solutions (a) and (b) were prepared in the following manner.

Solution (a)

70 g of a 10% by weight aqueous solution of bone gelatin (pH: 5.6 at 35° C.) was heated to 32° C. to dissolve.

Solution (b)

5 g of the above-described oleophilic polymer ultraviolet ray absorbing agent was dissolved in 20 g of ethyl acetate at 38° C., and a 70% by weight methanol solution of sodium dodecylbenzenesulfonate was added thereto.

Then solutions (a) and (b) were put in a mixer with explosion preventing equipment. After stirring for 1 minute at a high speed, the operation of the mixer was stopped and the ethyl acetate was distilled off under a reduced pressure. Thus, the latex wherein the oleophilic polymer ultraviolet ray absorbing agent was dispersed in a diluted aqueous solution of gelatin was obtained.

SYNTHESIS EXAMPLE 11

Synthesis of oleophilic polymer ultraviolet ray absorbing agent (2)

63 g of ultraviolet ray absorbing monomer (5) and 27 g of methyl methacrylate were dissolved in 450 ml of dioxane. While stirring the resulting solution by heating at 70° C. under a nitrogen stream, a solution prepared by dissolving 810 mg of 2,2'-azobis-(2,4-dimethylvaleronitrile) in 15 ml of dioxane was added, and the reaction was carried out for 5 hours. Then, the resulting product was poured into 5 l of ice water, and the solid thus-separated was collected by filtration and thoroughly washed with water and then methanol. The product was dried to obtain 78 g of the oleophilic polymer ultraviolet ray absorbing agent. As a result of nitrogen analysis of the oleophilic polymer ultraviolet ray absorbing agent, it was found that the copolymer synthesized contained 66.3% of the ultraviolet ray absorbing monomer unit.

$\lambda_{max}^{CH3COOC2H5} = 315$ nm.

Process for preparing ultraviolet ray absorbing polymer latex (B)

Polymer latex (B) was prepared in the same procedure as that for the above described Polymer Latex (A).

SYNTHESIS EXAMPLE 12

Synthesis of Copolymer Latex of Compound (26) and methyl methacrylate 7 liters of an aqueous solution containing 150 g of sodium salt of oleylmethyltauride was heated to 90° C. while slowly passing a nitrogen stream therethrough under stirring. To the resulting mixture, 100 ml of an aqueous solution containing 5.6 g of potassium persulfate was added. Then, 600 g of ultraviolet ray absorbing monomer (1) and 120 g of methyl methacrylate were dissolved in 1 liter of ethanol, and the resulting solution was added to the mixture. After the completion of the addition, the mixture was stirred for 1 hour while heating at 85° to 90° C., and 30 ml of an aqueous solution containing 2.2 g of potassium persulfate was added thereto. After the reaction was further carried out for 1 hour, the ethanol and the methyl methacrylate not reacted were distilled off as an azeotropic mixture with water. The latex thus-formed was cooled. After the pH was adjusted to 6.0 with a 1N sodium hydroxide solution, the latex was filtered. The concentration of the copolymer in the latex was 10.03%. As a result of nitrogen analysis it was found that the copolymer synthesized contained 76.7% of the ultraviolet ray absorbing monomer unit. Further, the latex had the absorption maximum at 381 nm in the aqueous system.

SYNTHESIS EXAMPLE 13

Synthesis of Oleophilic polymer ultraviolet ray absorbing agent (3)

21 g of ultraviolet ray absorbing monomer (28) and 9 g of methyl acrylate were dissolved in 150 ml of dioxane. While stirring the resulting solution with heating at 70° C. under a nitrogen stream, a solution prepared by dissolving 270 mg of 2,2'-azobis-(2,4-dimethylvaleronitrile) in 5 ml of dioxane was added, and the reaction was carried out for 5 hours. Then, the resulting product was poured into 2 liters of ice water, and the solid thus-separated was collected by filtration and thoroughly washed with water. The product was dried to obtain 23.9 g of the oleophilic polymer ultraviolet ray absorbing agent. As a result of nitrogen analysis of the oleophilic polymer ultraviolet ray absorbing agent, it was found that the copolymer synthesized contained 63.1% of the ultraviolet ray absorbing monomer unit.

$\lambda_{max}^{CH_3COOC_2H_5} = 372$ nm.

Process for preparing ultraviolet ray absorbing polymer latex (C)

Two solutions (i) and (ii) were prepared in the following manner.

Solution (i)

70 g of a 10% by weight aqueous solution of bone gelation (pH: 5.6 at 35° C.) was heated to 32° C. to dissolve.

Solution (ii)

5 g of the above-described oleophilic polymer ultraviolet ray absorbing agent was dissolved in 20 g of ethyl acetate at 38° C., and a 70% by weight methanol solution of sodium dodecylbenzenesulfonate was added thereto.

Then, solutions (i) and (ii) were put into a mixer with explosion preventing equipment. After stirring for 1 minute at a high speed, the operation of the mixer was stopped and the ethyl acetate was distilled off under a reduced pressure. Thus, the latex wherein the oleophilic polymer ultraviolet ray absorbing agent was dispersed in a diluted aqueous solution of gelatin was obtained.

The ultraviolet ray absorbing polymer latex according to the present invention is used by adding it to the hydrophilic colloid layers of the silver halide photographic light-sensitive material, such as a surface protective layer, an intermediate layer or a silver halide emulsion layer, etc. It is preferred to use it in the surface protective layer or the hydrophilic colloid layer adjacent to the surface protective layer. Particularly, it is preferable to add it to the lower layer in the surface protective layer consisting of two layers.

The amount used of the ultraviolet ray absorbing polymer latex in the present invention is not restricted, but it is preferred to be in a range of 10 to 2,000 mg and preferably, 50 to 1,000 mg per square meter.

Preferred examples of the silver halide having a diameter of 0.2 microns or less which can be used in the present invention include silver chlorobromide, silver iodobromide and silver bromide. The crystal habit of the silver halide is not specifically restricted. Further, the degree of sensitivity of the fine grained silver halide used in the present invention is not particularly restricted, but it is preferred to be substantially light-insensitive. Previously fogged silver halide may be employed. Silver halide having a diameter of 0.15 microns or less is preferred.

The fine grained silver halide used in the present invention can be easily prepared by using methods known to one skilled in the art and described in literatures. For example, the descriptions in P. Glafkides, *Photographic Chemistry*, vol. 1, pages 365 to 368 (1958), Mees and James, *The Theory of the Photographic Process*, page 36 (1966), P. H. Cloford, "Small Scale Preparation of Fine Grain (Colloidal) Photographic Emulsion" in *Note on Applied Science*, vol. 20 (Published by The National Physical Laboratory, 1930), etc. can be referred to.

Also, the fine grained silver halide can be prepared by the methods as described in U.S. Pat. Nos. 3,801,326 and 3,737,017. Further, the so-called Lippmann type emulsion which contains extremely fine grained silver halides (having a diameter of 0.1 micron or less) can be employed. These Lippmann emulsions can be obtained by precipitation of silver halides in the presence of a compound, for example, a heterocyclic mercapto compound as described in British Patent No. 1,204,623, a heterocyclic mercapto precursor compound as described in West German Patent Application (OLS) No. 2,161,044, compounds as described in U.S. Pat. Nos. 3,661,592 and 3,704,130, or compounds as described in *Research Disclosure*, RD-9401 (Published by Industrial Opportunities Ltd., Havant, Hampshire, February, 1972).

In order to determine the size of fine grained silver halide in the present invention, conventional method can be used. For example, an electron microscopic photograph of fine grained silver halide to be determined is taken and grain size is expressed as a diameter of equivalent circle.

The fine grained silver halide according to the present invention can be added to at least one layer constituting the photographic light-sensitive material. It is preferred to add to a layer other than a silver halide emulsion layer, for example, a surface protective layer, or a back layer, etc. In the case that the back layer consists of two layers, it may be added to any of them. In the case that the surface protective layer consists of two layers, it may be added to any of them. In any event, it is preferred that the fine grained silver halide is added to a layer positioned on the same side of a support as a layer containing the ultraviolet ray absorbing polymer latex having a repeating unit derived from a monomer represented by the general formula (I) described above of the present invention.

The fine grained silver halide used in the present invention is added to a coating solution for a surface protective layer or a back layer, etc. and then, the coating solution is applied by a dip coating method, an air-knife coating method, or an extrusion coating method using a hopper as described in U.S. Pat. No. 2,681,294, or by a method described in U.S. Pat. Nos. 3,508,947, 2,941,898 and 3,526,528, etc., by which two or more layers are applied at the same time.

It is preferred that an amount of the fine grained silver halide according to the present invention be from 0.1 mg to 1.0 g, and particularly from 1 mg to 500 mg, per square meter of the photographic light-sensitive material. However, the above-described amount can vary according to the particular kind of photographic film base to be used, the photographic composition, and the form and method of coating.

Examples of the support used for the photographic light-sensitive material of the present invention include a cellulose nitrate film, a cellulose acetate film, a polystyrene film, a polyethylene terephthalate film, a polycarbonate film and a laminate thereof, etc. Further, it is possible to use paper coated or laminated with baryta or an α-olefin polymer, and particularly a polymer of α-olefin having from 2 to 10 carbon atoms such as polyethylene, etc.

In the photographic light-sensitive material of the present invention, each photographic constituting layer can contain a binder. Examples of useful binders include as a hydrophilic colloid a protein such as gelatin, colloidal albumin, casein, etc.; a cellulose compound such as carboxymethyl cellulose, hydroxyethyl cellulose, etc.; a saccharide such as a starch derivative, etc.; and a synthetic hydrophilic colloid, for example, polyvinyl alcohol, poly-N-vinylpyrrolidone, a polyacrylic acid copolymer, polyacrylamide, etc. If desired, these colloids can be used as a mixture of two or more thereof.

Among them, gelatin is most suitably employed. "Gelatin" as used herein means the so-called lime treated gelatin, acid treated gelatin, and enzyme treated gelatin.

The silver halide emulsion for the photographic light-sensitive material used in the present invention are usually prepared by mixing a solution of a water-soluble silver salt (for example, silver nitrate) with a solution of a water-soluble halide (for example, potassium bromide) in a presence of a solution of a water-soluble high molecular material such as gelatin. As the silver halide, it is possible to use not only silver chloride and silver bromide, but also a mixed silver halide such as silver chlorobromide, silver iodobromide, silver chloroiodobromide, etc.

The photographic emulsion can be subjected to spectral sensitization or supersensitization using a polymethine sensitizing dye such as cyanine, merocyanine, carbocyanine, etc., alone or as a combination thereof, or by using such a dye in combination with a styryl dye, etc., if desired.

Furthermore, it is possible to add various compounds to the photographic emulsion for the photographic light-sensitive material used in the present invention in order to prevent deterioration of sensitivity or the occurrence of fog in the step for production of the light-sensitive material, during preservation or during processing. Many such compounds have been known hitherto, examples of which include a heterocyclic compound including 4-hydroxy-6-methyl-1,3,3a,7-tetraazaindene, 3-methylbenzothiazole and 1-phenyl-5-mercaptotetrazole, a mercury containing compound, a mercapto compound, a metal salt, etc.

In the case of using the silver halide photographic emulsion as a color photographic light-sensitive material, the silver halide emulsion layer may contain a coupler. As such a coupler, it is possible to use a 4-equivalent diketomethylene yellow coupler, a 2-equivalent diketomethylene yellow coupler, a 4-equivalent or 2-equivalent pyrazolone magenta coupler, an indazolone magenta coupler, an α-naphthol cyan coupler, a phenol cyan coupler, etc.

The silver halide emulsion layer and other layers in the photographic light-sensitive material of the present invention can be hardened by various organic or inorganic hardening agents (alone or as a combination). Typical examples thereof include an aldehyde compound such as mucochloric acid, formaldehyde, trimethylolmelamine, glyoxal, 2,3-dihydroxy-1,4-dioxane, 2,3-dihydroxy-5-methyl-1,4-dioxane, succinaldehyde, and glutaraldehyde, etc.; an active vinyl compound such as divinyl sulfone, methylenebismaleimide, 1,3,5-triacryloyl-hexahydro-s-triazine, 1,3,5-trivinylsulfonyl-hexahydro-s-triazine, bis(vinylsulfonylmethyl)ether, 1,3-bis(vinylsulfonylmethyl)propanol-2, and bis(α-vinylsulfonylacetamido)ethane, etc.; an active halogen compound such as sodium salt of 2,4-dichloro-6-hydroxy-s-triazine and 2,4-dichloro-6-methoxy-s-triazine, etc.; and an ethyleneimine compound such as 2,4,6-triethyleneimino-s-triazine, etc.

A surface active agent may be added alone or as a mixture to the photographic constituting layer of the present invention. It may be used as a coating aid, but it can sometimes be used for other purposes, for example, for emulsification or dispersion, sensitization, or improvement of other photographic properties and control of triboelectric series.

These surface active agents are classified into a natural surface active agent such as saponin, etc.; a nonionic surface active agent such as alkylene oxide type, glycerine type or glycidol type active agent; a cationic surface active agent such as a higher alkylamine, a quaternary ammonium salt, pyridine and other heterocyclic compounds, a sulfonium compound, or a phosphonium compound, etc.; an anionic surface active agent containing an acid group such as a carboxylic acid, a sulfonic acid, a phosphoric acid, a sulfuric acid ester, or a phosphoric acid ester group, etc.; and an ampholytic surface active agent such as an amino acid, an aminosulfonic acid, or a sulfuric or phosphoric acid ester of aminoalcohol, etc.

In the present invention, a fluorine containing surface active agent can also be used. Examples of such fluorine containing surface active agents include the following compounds. For example, there are fluorine containing surface active agents as described in British Pat. Nos. 1,330,356 and 1,524,631, U.S. Pat. Nos. 3,666,478, 3,689,906 and 3,850,642, Japanese Patent Publication No. 26689/77 and Japanese Patent Application (OPI) Nos. 46733/74 and 32322/76, etc.

In the photographic light-sensitive material of the present invention, the photographic constituting layer may contain a polymer latex as described in U.S. Pat. Nos. 3,411,911 and 3,411,912, Japanese Patent Publication No. 5331/70, etc. or silica, strontium sulfate, barium sulfate or polymethyl methacrylate, etc., as a matting agent.

The photographic light-sensitive material of the present invention may contain a color forming coupler, namely, a compound capable of color forming by oxidative coupling with an aromatic primary amine developing agent (for example, a phenylenediamine derivative or an aminophenol derivative, etc.) by color development processing. Examples of the color forming couplers include a 5-pyrazolone coupler, a pyrazolobenzimidazole coupler, a cyanoacetylcoumarone coupler and an open-chain acylacetonitrile coupler, etc. as a magenta coupler; an acylacetamide coupler (for example, a benzoylacetanilide and a pivaloyl acetanilide), etc. as a yellow coupler; and a naphthol coupler and a phenol coupler, etc. as a cyan coupler. The coupler is preferred to have a hydrophobic group called a ballast group in the molecule so as to be non-diffusible. The coupler may be any of 4-equivalence and 2-equivalence to silver ion. Further, the coupler may be a colored coupler having an effect of color correction or a coupler which releases a development inhibitor by development (the so-called DIR coupler).

Further, a non-color-forming DIR coupling compound which produces a colorless product by coupling reaction and releases a developing inhibitor may be contained other than the DIR coupler.

The photographic light-sensitive material of the present invention may contain a hydroquinone derivative, an amino phenol derivative, a gallic acid derivative, an ascorbic acid derivative, etc. as a color fog preventing agent.

When practicing the present invention, the following known fading preventing agents can be used together. Further, color image stabilizers used in the present invention may be alone or a combination of two or more thereof. Examples of known fading preventing agents include a hydroquinone derivative, a gallic acid derivative, a p-alkoxyphenol, a p-oxyphenol derivative and a bisphenol.

The present invention is preferably applied to a multilayer color photographic material comprising at least two layers having each a different spectral sensitivity on a support. The multilayer color photographic material generally has at least one red-sensitive emulsion layer, at least one green-sensitive emulsion layer and at least one blue-sensitive emulsion layer on the support. The order of these layers can be suitably selected as occasion demands. Usually, the red-sensitive emulsion layer contains a cyan forming coupler, the green-sensitive emulsion layer contains a magenta forming coupler and the blue-sensitive emulsion layer contains a yellow forming coupler, but other combinations may be adopted, if necessary.

Photographic processing of the photographic light-sensitive material of the present invention can be carried out by any known methods. Known processing solutions can be used. The processing temperature is generally selected from a range of 18° C. to 50° C., but a temperature lower than 18° C. or a temperature higher than 50° C. may be used, too. Any of a development processing for forming silver images (black-and-white photographic processing) and a color photographic processing comprising a development processing for forming dye images can be adopted as occasion demands.

The color developing solution generally comprises an aqueous alkaline solution containing a color developing agent. The color developing agents which can be used include known primary aromatic amine developing agents, for example, a phenylenediamine (for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline and 4-amino-3-methyl-N-ethyl-N-$\beta$-methoxyethylaniline, etc.).

In addition, it is possible to use compounds described in L. F. A. Mason, *Photographic Processing Chemistry* (issued by Focal Press, 1966) pages 226–229, U.S. Pat. Nos. 2,193,015 and 2,592,364 and Japanese Patent Application (OPI) No. 64933/73, etc.

According to the present invention, problems originating from static charges generating during the steps for production of the photographic light-sensitive material and/or in the case of using the photographic light-sensitive material can be overcome.

For example, formation of static marks caused by contact of the emulsion surface of the photographic light-sensitive material with the back surface, contact of the emulsion surface with another emulsion surface, or contact of the emulsion surface with a material which frequently contacts with the photographic light-sensitive material, such as rubber, metal, plastics, fluorescent sensitizing paper, etc., is remarkably reduced by carrying out the present invention.

In the following, the effects of the present invention are illustrated in detail by reference to Examples, but the present invention is not to be construed as being limited thereto.

EXAMPLE 1

A multilayer color photographic light-sensitive material comprising layers having the compositions described below on a polyethylene terephthalate film support was prepared.

The 1st Layer: Antihalation layer (AHL)
  A gelatin layer containing black colloidal silver.
The 2nd Layer: Intermediate layer (ML)
  A gelatin layer containing an emulsified dispersion of 2,5-di-tert-octylhydroquinone.
The 3rd Layer: The first red-sensitive emulsion layer ($RL_1$)
  Silver iodobromide emulsion (silver iodide: 5% by mol) Amount of silver coated: 1.79 g/m$^2$
  Sensitizing dye I: $6 \times 10^{-5}$ mol per mol of silver
  Sensitizing dye II: $1.5 \times 10^{-5}$ mol per mol of silver
  Coupler A: 0.04 mol per mol of silver
  Coupler C-1: 0.0015 mol per mol of silver
  Coupler C-2: 0.0015 mol per mol of silver
  Coupler D: 0.0006 mol per mol of silver
The 4th Layer: The second red-sensitive emulsion layer ($RL_2$)
  Silver iodobromide emulsion (silver iodide: 4% by mol) Amount of silver coated: 1.4 g/m$^2$
  Sensitizing dye I: $3 \times 10^{-5}$ mol per mol of silver
  Sensitizing dye II: $1.2 \times 10^{-5}$ mol per mol of silver
  Coupler A: 0.02 mol per mol of silver
  Coupler C-1: 0.0008 mol per mol of silver
  Coupler C-2: 0.0008 mol per mol of silver
The 5th Layer: Intermediate layer (ML)
  The same as the 2nd layer.
The 6th Layer: The first green-sensitive emulsion layer ($GL_1$)
  Silver iodobromide emulsion (silver iodide: 4% by mol) Amount of silver coated: 1.5 g/m$^2$
  Sensitizing dye III: $3 \times 10^{-5}$ mol per mol of silver
  Sensitizing dye IV: $1 \times 10^{-5}$ mol per mol of silver
  Coupler B: 0.05 mol per mol of silver
  Coupler M-1: 0.008 mol per mol of silver
  Coupler D: 0.0015 mol per mol of silver
The 7th Layer: The second green-sensitive emulsion layer ($GL_2$)
  Silver iodobromide emulsion (silver iodide: 5% by mol) Amount of silver coated: 1.6 g/m$^2$
  Sensitizing dye III: $2.5 \times 10^{-5}$ mol per mol of silver
  Sensitizing dye IV: $0.8 \times 10^{-5}$ mol per mol of silver
  Coupler B: 0.02 mol per mol of silver
  Coupler M-1: 0.003 mol per mol of silver
  Coupler D: 0.0003 mol per mol of silver
The 8th Layer: Yellow filter layer (YFL)
  A gelatin layer containing yellow colloidal silver and an emulsified dispersion of 2,5-di-tert-octylhydroquinone in an aqueous solution of gelatin.
The 9th Layer: The first blue-sensitive emulsion layer ($BL_1$)
  Silver iodobromide emulsion (silver iodide: 6% by mol) Amount of silver coated: 1.5 g/m$^2$
  Coupler Y-1: 0.25 mol per mol of silver
The 10th Layer: The second blue-sensitive emulsion Layer ($BL_2$)
  Silver iodobromide (silver iodide: 6% by mol) Amount of silver coated: 1.1 g/m$^2$
  Coupler Y-1: 0.06 mol per mol of silver
The 11th Layer: Protective under layer (PUL)
  Gelatin: 1.0 g/m$^2$
  Coating Aid $C_8H_{17}$—⟨phenyl⟩—$(OCH_2CH_2)_3$—$SO_3Na$   5 mg/m² n-Octyl-5-(N,N-diethylamino)-2-phenylsulfonyl-
2,4-pentanedienoate: 150 mg/m²

The 12th Layer: Protective Over Layer (POL)
 Gelatin: 0.7 g/m²
 Polymethyl methacrylate (average particle size: 2.5
  microns): 20 mg/m²
 Coating Aid (the same as used in PUL)

$$C_8F_{17}SO_2\underset{\underset{C_3H_7}{|}}{N}CH_2COOK \quad 12\ mg/m^2$$

Compounds used for preparing the samples:

Sensitizing dye I: Anhydro-5,5'-dichloro-3,3'-di(γ-sulfopropyl)-9-ethylthiacarbocyanine hydroxide pyridinium salt.

Sensitizing dye II: Anhydro-9-ethyl-3,3'-di(γ-sulfopropyl)-4,5,4',5'-dibenzothiacarbocyanine hydroxide triethylamine salt.

Sensitizing dye III: Anhydro-9-ethyl-5,5'-dichloro-3,3'-di(γ-sulfopropyl)oxacarbocyanine sodium salt.

Sensitizing dye VI: Anhydro-5,6,5',6'-tetrachloro-1,1'-diethyl-3,3'-di{β-[β-(γ-sulfopropoxy)ethoxy]-ethyl}-imidazolocarbocyanine hydroxide sodium salt.

Coupler A

Coupler B

Coupler C-1

Coupler C-2

Coupler D

Coupler M-1

Coupler Y-1

The above described sample was designated Sample I.

Into the 11th layer of Sample I, 2.5 mg/m² of a Lippmann type silver iodobromide (silver iodide: 1.5 mol %) emulsion having an average particle size of 0.07 μm and further an ultraviolet absorbing agent as shown in Table 1 below were incorporated to prepare Samples II to IX.

Emulsified Dispersion (C), (D) and (E) used for comparison were prepared in the manner described below. Ultraviolet Ray Absorbing Compound (60) has the following structure.

Ultraviolet Ray Absorbing Compound (60)

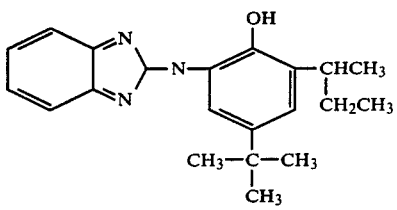

Preparation of Emulsified Dispersion (C)

Two kinds of solutions (a) and (b) were prepared in the following manner.

Solution (a)

1,000 g of a 10% by weight aqueous solution of bone gelatin (pH: 5.6 at 35° C.) was heated to 40° C. to dissolve.

Solution (b)

27.4 g of the above-described Ultraviolet Ray Absorbing Monomer (8) was dissolved in a solvent mixture composed of 40 g of dibutyl phthalate and 135 g of ethyl acetate as an auxiliary solvent at 38° C., and 23 g of a 72% by weight methanol solution of sodium dodecylbenzenesulfonate was added to the resulting solution.

Then, solutions (a) and (b) were put into a mixer with explosion preventing equipment. After being stirred for 1 minute at a high speed, the operation of the mixer was stopped and the ethyl acetate was distilled off under a reduced pressure. Thus, an Emulsified Dispersion (C) of Monomer (8) was prepared.

Emulsified Dispersions (D) and (E) were prepared using 28.7 g of Ultraviolet Ray Absorbing Monomer (5) and 46.4 g of Ultraviolet Ray Absorbing Compound (60) in the same procedure as described in Emulsified Dispersion (C), respectively.

In the preparation of emulsified dispersions of Monomers (5) and (8) and Compound (60), if dibutyl phthalate was not used, coarse crystals were separated within a very short time after emulsification, whereby not only the ultraviolet ray absorbing property varied but also the coating property remarkably deteriorated.

With respect to these samples, an antistatic property and an antiadhesive property were measured by the following methods, and the results shown in Table 1 below were obtained.

Antistatic Property

After the unexposed samples were conditioned at 25° C. and 5% RH for 24 hours, they were subjected to friction by rubbing reciprocally ten times using a rubber roller and a nylon bar in a dark room under the same conditioning condition as described above. Thereafter, they were subjected to the development processing described below, and the occurrence of static marks was examined.

| Development Processing Step | Time |
|---|---|
| 1. Color development | 3 minutes and 15 seconds |
| 2. Bleaching | 6 minutes and 30 seconds |
| 3. Washing with water | 3 minutes and 15 seconds |
| 4. Fixing | 6 minutes and 30 seconds |
| 5. Washing with water | 3 minutes and 15 seconds |
| 6. Stabilizing | 3 minutes and 15 seconds |

The compositions of the processing solutions used in each step were as follows.

| Color Developing Solution: | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—ethyl-N—β-hydroxyethylamino)-2-methylaniline sulfate | 4.5 g |
| Water to make | 1 liter |
| Bleaching Solution: | |
| Ammonium bromide | 160.0 g |
| Aqueous ammonia solution (28%) | 25.0 ml |
| Sodium ethylenediaminetetraacetato iron complex | 130.0 g |
| Glacial acetic acid | 14.0 ml |
| Water to make | 1 liter |
| Fixing Solution: | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 liter |
| Stabilizing Solution: | |
| Formalin | 8.0 m |
| Water to make | 1 liter |

Antiadhesion Test

A sample was cut in a size of 35 square mm. After the strips were conditioned for 1 day under a condition of 25° C. and 90% RH in such a state that each of them did not contact one another, they were preserved in such a state that the emulsion face was in contact with the back face under a condition of 40° C. and 90% RH for 2 days while applying a weight of 500 g. The films taken out were separated and the % area of the adhesion part was measured.

Valuations A-D are as follows.
A: Adhesion area: 0–40%
B: Adhesion area: 40–60%
C: Adhesion area: 60–80%
D: Adhesion area: more than 80%

The results thus obtained are shown in Table 1.

TABLE 1

| Sample | Composition of the 11th Layer | | Occurrence of Static Marks | | Antiadhesive Property |
| | Ultraviolet Ray Absorbing Agent | Fine Grained Silver Halide | Rubber | Nylon | |
|---|---|---|---|---|---|
| I (Control) | none | none | D | D | A |
| II (Present Invention) | Polymer Latex (A) | present | A | A | A |
| III (Present Invention) | Polymer Latex (B) | present | A | A | A |

TABLE 1-continued

| Sample | Composition of the 11th Layer | | Occurrence of Static Marks | | Antiadhesive Property |
| | Ultraviolet Ray Absorbing Agent | Fine Grained Silver Halide | Rubber | Nylon | |
| --- | --- | --- | --- | --- | --- |
| IV (Comparison) | Emulsified Dispersion (C) Monomer (8) | present | B | B | C |
| V (Comparison) | Emulsified Dispersion (D) Monomer (5) | present | B | B | C |
| VI (Comparison) | Emulsified Dispersion (E) Compound (60) | present | B | B | C |
| VII (Comparison) | none | present | D | D | A |
| VIII (Comparison) | Polymer Latex (A) | none | C | C | A |
| IX (Comparison) | Polymer Latex (B) | none | C | C | A |

In Table 1 above, evaluation of the occurrence of static marks was carried out according to the following four stages:

A: The occurrence of static marks was not observed.
B: The occurrence of static marks was slightly observed.
C: The occurrence of static marks was considerably observed.
D: The occurrence of static marks was observed on nearly the whole surface.

As is apparent from the results shown in Table 1, the samples which were endowed with antistatic property using the combination of the ultraviolet ray absorbing polymer latex and the fine grained silver halide according to the present invention show not only excellent antistatic effects so that the occurrence of static marks was hardly observed but also good antiadhesive properties.

EXAMPLE 2

Into the PU layer of Sample I described in Example 1, 1.4 cc/m² of Homopolymer Latex of Compound (5) as described in Synthesis Example 6, 1.6 cc/m² of Copolymer Latex of Compound (8) and n-butyl acrylate as described in Synthesis Example 7, 2.1 cc/m² of copolymer of Monomer (61) described below and butyl acrylate (3:1 ratio by weight) containing 7.32% of solid concentration which was prepared in the same manner as described in Synthesis Example 7, and an emulsion dispersion prepared in the same manner as described in Preparation of Emulsified Dispersion (C) in Example 1 except using 29.7 g of Monomer (61) in place of Monomer (8) were incorporated as shown in Table 2 below, respectively.

Monomer (61)

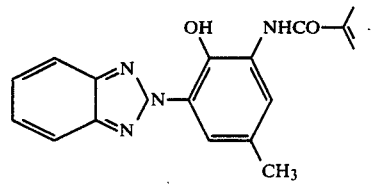

Further, a silver iodobromide (silver iodide: 2.0 mol %) emulsion having an average particle size of 0.1 μm which was prepared by a controlled double jet process was added in an amount of 300 mg/m² to a PO layer to prepare Samples X, XI, XII and XIII.

The antistatic property and the antiadhesive property of these samples were determined in the same manner as described in Example 1, and the results shown in Table 2 below were obtained.

As is apparent from the results shown in Table 2, of these samples only the samples in which the ultraviolet ray absorbing polymer latex and the fine grained silver halide are used according to the present invention satisfy both the antistatic property and the antiadhesive property.

TABLE 2

| Sample | Ultraviolet Ray Absorbing Agent in PU layer | Fine Grained Silver Halide in PO layer | Occurrence of Static Marks | | Antiadhesive Property |
| | | | Rubber | Nylon | |
| --- | --- | --- | --- | --- | --- |
| I (Control) | none | none | D | D | A |
| X (Present Invention) | P-5 | present | A | A | A |
| XI (Present Invention) | P-41 | present | A | A | A |
| XII (Comparison) | Copolymer Latex of Monomer (61) and Butyl Acrylate (3:1) | present | B | B | A |
| XIII (Comparison) | Emulsified Dispersion of Monomer (61) | present | B | C | C |

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising:
a support having thereon;

at least one light-sensitive silver halide emulsion layer; and at least one light-insensitive hydrophilic colloid layer;

wherein at least one of a surface protective layer, an intermediate layer or a silver halide emulsion layer contains (A) an ultraviolet ray absorbing polymer latex which comprises a polymer or copolymer having a repeating unit derived from a monomer represented by the following general formula (I):

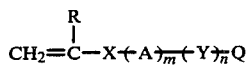

herein R represents a hydrogen atom, a lower alkyl group having from 1 to 4 carbon atoms or a chlorine atom; X represents —CONH—, —COO— or a phenylene group; A represents a linking group selected from an alkylene group having from 1 to 20 carbon atoms; Y represents —COO—, —OCO—, —CONH—, —NHCO—, —$SO_2$NH—, —NH$SO_2$—, —$SO_2$— or —O—; m represents 0 or an integer of 1; n represents 0 or an integer of 1; and Q represents an ultraviolet ray absorbing group represented by a general formula selected from the group consisting of (II) and (III):

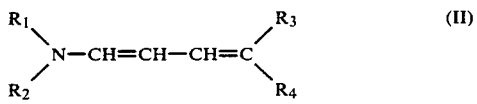

wherein $R_1$ and $R_2$, which may be the same or different, each represents a hydrogen atom, an alkyl group having from 1 to 20 carbon atoms or an aryl group having from 6 to 20 carbon atoms, provided that the both of $R_1$ and $R_2$ do not simultaneously represent hydrogen atoms, and further $R_1$ and $R_2$ may combine to form an atomic group necessary to form a cyclic amino group; $R_3$ represents a cyano group, —COO$R_5$, —CONH$R_5$, —COR$_5$ or —$SO_2R_5$; and $R_4$ represents a cyano group, —COO$R_6$, —CONH$R_6$, —COR$_6$, or —$SO_2R_6$; wherein $R_5$ and $R_6$ each represents an alkyl group having from 1 to 20 carbon atoms or an aryl group having from 6 to 20 carbon atoms, and further $R_5$ and $R_6$ may combine to form an atomic group necessary to form a 1,3-dioxocyclohexane nucleus, a 1,3-diaza-2,4,6-trioxocyclohexane nucleus (a barbituric acid nucleus), a 1,2-diaza-3,5-dioxocyclopentane nucleus or a 2,4-diaza-1-alkoxy-3,5-dioxocyclohexene nucleus; and at least one of $R_1$, $R_2$, $R_3$ and $R_4$ bonds to the vinyl group through the linking group;

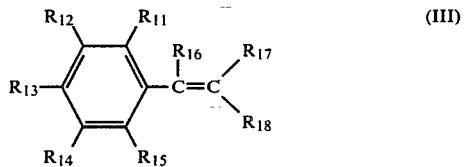

wherein $R_{11}$, $R_{12}$, $R_{13}$, $R_{14}$, $R_{15}$ each represents a hydrogen atom, a halogen atom, an alkyl group having from 1 to 20 carbon atoms, an aryl group having from 6 to 20 carbon atoms, an alkoxy group having from 1 to 20 carbon atoms, an aryloxy group having from 6 to 20 carbon atoms, an alkylthio group having from 1 to 20 carbon atoms, an arylthio group having from 6 to 20 carbon atoms, an amino group, an alkylamino group having from 1 to 20 carbon atoms, an arylamino group having from 6 to 20 carbon atoms, a hydroxyl group, a cyano group, a nitro group, an acylamino group, a carbamoyl group, a sulfonyl group, a sulfamoyl group, a sulfonamide group, an acyloxy group or an oxycarbonyl group, and $R_{11}$ and $R_{12}$, $R_{12}$ and $R_{13}$, $R_{13}$ and $R_{14}$ or $R_{14}$ and $R_{15}$ may form a 5- or 6-membered ring by ring closure; $R_{16}$ represents a hydrogen atom or an alkyl group having from 1 to 20 carbon atoms; $R_{17}$ represents a cyano group, —COO$R_{19}$, —CONH$R_{19}$, —COR$_{19}$ or —$SO_2R_{19}$; $R_{18}$ represents a cyano group, —COO$R_{20}$, —CONH$R_{20}$, —COR$_{20}$ or —$SO_2R_{20}$; wherein $R_{19}$ and $R_{20}$ each represents an alkyl group having from 1 to 20 carbon atoms or an aryl group having from 6 to 20 carbon atoms; wherein one of $R_{11}$, $R_{12}$, $R_{13}$, $R_{14}$, $R_{15}$, $R_{16}$, $R_{17}$ and $R_{18}$ bonds to the vinyl group through the linking group;

wherein a fine grained silver halide having a diameter of 0.2 microns or less is present in a photographic layer other than a silver halide emulsion layer; and wherein the ultraviolet ray absorbing polymer latex is present in an amount within the range of from 10 to 2,000 mg/m$^2$ of the material.

2. A silver halide photographic light-sensitive material as claimed in claim 1, wherein $R_1$ and $R_2$ each represents an alkyl group having from 1 to 20 carbon atoms; $R_3$ represents a cyano group or —$SO_2R_5$; $R_4$ represents a cyano group or —COO$R_6$; and $R_5$ and $R_6$ each represents an alkyl group having from 1 to 20 carbon atoms or an aryl group having from 6 to 20 carbon atoms.

3. A silver halide photographic light-sensitive material as claimed in claim 1, wherein $R_1$ and $R_2$ each represents an alkyl group having from 1 to 6 carbon atoms; $R_3$ represents —$SO_2R_5$; $R_4$ represents —COO$R_6$; $R_5$ represents a phenyl group which may be substituted; and $R_6$ represents an alkyl group having from 1 to 20 carbon atoms.

4. A silver halide photographic light-sensitive material as claimed in claim 1, wherein $R_{11}$, $R_{12}$, $R_{13}$, $R_{14}$ and $R_{15}$ each represents a hydrogen atom, a halogen atom, an alkyl group having from 1 to 20 carbon atoms, an aryl group having from 6 to 20 carbon atoms, an alkoxy group having from 1 to 20 carbon atoms, an aryloxy group having from 6 to 20 carbon atoms, an alkylamino group having from 1 to 20 carbon atoms, an arylamino group having from 6 to 20 carbon atoms, a hydroxy group, an acylamino group, a carbamoyl group, an acyloxy group or an oxycarbonyl group, and $R_{11}$ and $R_{12}$, $R_{12}$ and $R_{13}$, $R_{13}$ and $R_{14}$ or $R_{14}$ and $R_{15}$ may form a 5- or 6-membered ring by ring closure; $R_{16}$ represents a hydrogen atom or an alkyl group having from 1 to 20 carbon atoms; $R_{17}$ represents a cyano group, —COO$R_{19}$, —CONH$R_{19}$, —COR$_{19}$ or —$SO_2R_{19}$; and $R_{18}$ represents a cyano group, —COO$R_{20}$, —CONH$R_{20}$, —COR$_{20}$ or —$SO_2R_{20}$; wherein $R_{19}$ and $R_{20}$ each represents an alkyl group having from 1 to 20 carbon atoms or an aryl group having from 6 to 20 carbon atoms; and at least one of $R_{11}$, $R_{12}$, $R_{13}$, $R_{14}$, $R_{15}$, $R_{16}$, $R_{17}$ and $R_{18}$ bonds to the vinyl group through the linking group.

5. A silver halide photographic light-sensitive material as claimed in claim 1, wherein R represents a hydrogen atom, a lower alkyl group having from 1 to 4 carbon atoms or a chlorine atom; X represents —COO—; m and n each represents 0; and Q represents an ultraviolet ray absorbing group represented by the general formula (III); wherein $R_{11}$, $R_{12}$, $R_{14}$ and $R_{15}$ each represents a hydrogen atom; $R_{13}$ represents a hydrogen atom or an alkyl group having from 1 to 5 carbon atoms; $R_{16}$ represents a hydrogen atom; $R_{17}$ represents a cyano group; and $R_{18}$ represents —COOR$_{20}$; wherein $R_{20}$ represents an alkylene group having from 1 to 20 carbon atoms which bonds to the vinyl group.

6. A silver halide photographic light-sensitive material as claimed in claim 1, wherein the ultraviolet ray absorbing polymer latex comprises a homopolymer having a repeating unit derived from the monomer represented by the general formula (I).

7. A silver halide photographic light-sensitive material as claimed in claim 1, wherein the ultraviolet ray absorbing polymer latex comprises a copolymer of the monomer represented by the general formula (I) with a copolymerizable monomer.

8. A silver halide photographic light-sensitive material as claimed in claim 7, wherein the copolymerizable monomer is an acrylic acid ester, an acrylic acid amide, a vinyl ester, an acrylonitrile, an aromatic vinyl compound, itaconic acid, citraconic acid, crotonic acid, vinylidene chloride, a vinyl alkyl ether, a maleic acid ester, N-vinylpyrrolidone, N-vinylpyridine, or 2- or 4-vinylpyridine.

9. A silver halide photographic light-sensitive material as claimed in claim 7, wherein the copolymerizable monomer is an acrylic acid ester, a methacrylic acid ester or an aromatic vinyl compound.

10. A silver halide photographic light-sensitive material as claimed in claim 1, wherein the ultraviolet ray absorbing polymer latex is a latex prepared by emulsion polymerization of monomers comprising the monomer represented by the general formula (I).

11. A silver halide photographic light-sensitive marterial as claimed in claim 1, wherein the ultraviolet ray absorbing polymer latex is a latex prepared by dissolving an oleophilic polymer ultraviolet ray absorbing agent obtained by polymerization of monomers comprising the monomer represented by the general formula (I) in an organic solvent and then dispersing the solution in a latex form in an aqueous gelatin solution.

12. A silver halide photographic light-sensitive material as claimed in claim 1, wherein the amount of the ultraviolet ray absorbing agent portion in the polymer latex is from 5 to 100% by weight.

13. A silver halide photographic light-sensitive material as claimed in claim 1, wherein the amount of the ultraviolet ray absorbing agent portion in the polymer latex is from 50 to 100% by weight.

14. A silver halide photographic light-sensitive material as claimed in claim 1, wherein the ultraviolet ray absorbing polymer latex is present in a surface protective layer or a hydrophilic colloid layer adjacent to the surface protective layer.

15. A silver halide photographic light-sensitive material as claimed in claim 14, wherein the surface protective layer is composed of two separate layers and the lower layer thereof contains the ultraviolet ray absorbing polymer latex.

16. A silver halide photographic light-sensitive material as claimed in claim 1, wherein the ultraviolet ray absorbing polymer latex is present in an amount within the range of from 50 to 1,000 mg/m² of the material.

17. A silver halide photographic light-sensitive material as claimed in claim 1, wherein the fine grained silver halide is silver chlorobromide, silver iodobromide or silver bromide.

18. A silver halide photographic light-sensitive material as claimed in claim 1, wherein the fine grained silver halide is substantially light-insensitive.

19. A silver halide photographic light-sensitive material as claimed in claim 1, wherein the fine grained silver halide has a diameter of 0.15 microns or less.

20. A silver halide photographic light-sensitive material as claimed in claim 1, wherein the fine grained silver halide is a Lippmann type emulsion having a grain size of 0.1 micron or less.

21. A silver halide photographic light-sensitive material as claimed in claim 1, wherein the fine grained silver halide is present in a surface protective layer or a back layer.

22. A silver halide photographic light-sensitive material as claimed in claim 15, wherein the lower layer also contains the fine grained silver halide.

23. A silver halide photographic light-sensitive material as claimed in claim 15, wherein the upper layer thereof contains the fine grained silver halide.

24. A silver halide photographic light-sensitive material as claimed in claim 1, wherein the fine grained silver halide is present in an amount within the range of from 0.1 mg/m² to 1.0 g/m² of the material.

25. A silver halide photographic light-sensitive material as claimed in claim 1, wherein the fine grained silver halide is present in an amount within the range from 1 mg/m² to 500 mg/m² of the material.

26. A silver halide photographic light-sensitive material as claimed in claim 1, wherein the photographic light-sensitive material further contains a color forming coupler.

27. A silver halide photographic light-sensitive material as claimed in claim 1, wherein the photographic light-sensitive material comprises a red-sensitive silver halide emulsion layer, a green-sensitive silver halide emulsion layer and a blue-sensitive silver halide emulsion layer.

28. A multilayer color photographic light-sensitive material comprising:
 a support having thereon;
 a red-sensitive silver halide emulsion layer containing a cyan forming coupler;
 a green-sensitive halide emulsion layer containing a magenta forming coupler;
 a blue-sensitive silver halide emulsion layer containing a yellow forming coupler; and
 a light-insensitive layer, wherein at least one of a surface protective layer, an intermediate layer or a silver halide emulsion layer contains an ultraviolet ray absorbing polymer latex which comprises a polymer having a repeating unit derived from a monomer represented by the following general formula (I):

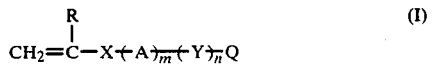
(I)

wherein R represents a hydrogen atom, a lower alkyl group having from 1 to 4 carbon atoms or a chlorine atom; X represents —CONH—, —COO— or a phenylene group; A represents a linking group selected from an alkylene group having from 1 to 20 carbon atoms or an arylene group having from 6 to 20 carbon atoms; Y represents —COO—, —OCO—, —CONH—, —NHCO—, —SO$_2$NH—, —NHSO$_2$— —SO$_2$— or —O—; m represents 0 or an integer of 1; n represents 0 or an integer of 1; and Q represents an ultraviolet ray absorbing group represented by a general formula selected from the group consisting of (II) and (III):

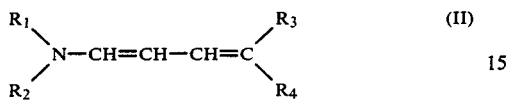

wherein R$_1$ and R$_2$, which may be the same or different, each represents a hydrogen atom, an alkyl group having from 1 to 20 carbon atoms or an aryl group having from 6 to 20 carbon atoms, provided that the both of R$_1$ and R$_2$ do not simultaneously represented hydrogen atoms, and further R$_1$ and R$_2$ may combine to form an atomic group necessary to form a cyclic amino group; R$_3$ represents a cyano group, —COOR$_5$—, —CONHR$_5$—, —COR$_5$ or —SO$_2$R$_5$; and R$_4$ represents a cyano group, —COOR$_6$, —CONHR$_6$, —COR$_6$ or —SO$_2$R$_6$; wherein R$_5$ and R$_6$ each represents an alkyl group having from 1 to 20 carbon atoms or an aryl group having from 6 to 20 carbon atoms, and further R$_5$ and R$_6$ may combine to form an atomic group necessary to form a 1,3-dioxocyclohexane nucleus, a 1,3-diaza-2,4,6-trioxocyclohexane nucleus (a barbituric acid nucleus), a 1,2-diaza-3,5-dioxocyclopentane nucleus or a 2,4-diaza-1-alkoxy-3,5-dioxocyclohexene nucleus; and at least one of R$_1$, R$_2$, R$_3$, and R$_4$ bonds to the vinyl group through the linking group

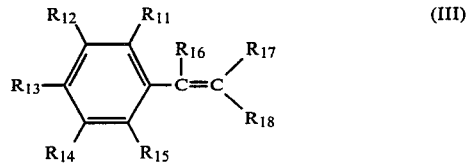

wherein R$_{11}$, R$_{12}$, R$_{13}$, R$_{14}$ and R$_{15}$ each represents a hydrogen atom, a halogen atom, an alkyl group having from 1 to 20 carbon atoms, an aryl group having from 6 to 20 carbon atoms, an alkoxy group having from 1 to 20 carbon atoms, an aryloxy group having from 6 to 20 carbon atoms, an alkylthio group having from 1 to 20 carbon atoms, an arylthio group having from 6 to 20 carbon atoms, an amino group, an alkylamino group having from 1 to 20 carbon atoms, an arylamino group having from 6 to 20 carbon atoms, a hydroxyl group, a cyano group, a nitro group, an acylamino group, a carbamoyl group, a sulfonyl group, a sulfamoyl group, a sulfonamide group, an acyloxy group or an oxycarbonyl group, and R$_{11}$ and R$_{12}$, R$_{12}$ and R$_{13}$, R$_{13}$ and R$_{14}$ or R$_{14}$ or R$_{14}$ and R$_{15}$ may form a 5- or 6-membered ring by ring closure; R$_{16}$ represents a hydrogen atom or an alkyl group having from 1 to 20 carbon atoms; R$_{17}$ represents a cyano group, —COOR$_{19}$, —CONHR$_{19}$, —COR$_{19}$ or —SO$_2$R$_{19}$; and R$_{18}$ represents a cyano group, —COOR$_{20}$, —CONHR$_{20}$, —COR$_{20}$ or —SO$_2$R$_{20}$; wherein R$_{19}$ and R$_{20}$ each represents an alkyl group having from 1 to 20 carbon atoms or an aryl group having from 6 to 20 carbon atoms; wherein one of R$_{11}$, R$_{12}$, R$_{13}$, R$_{14}$, R$_{15}$, R$_{16}$, R$_{17}$ and R$_{18}$ bonds to the vinyl group through the linking group;

wherein a fine grain silver halide having a diameter of 0.2 microns or less is present in a photographic layer obtain than a silver halide emulsion layer; and wherein the ultra violet ray absorbing polymer latex is present in an amount within the range of from 10 to 2,000 mg/m$^2$ of the material.

* * * * *

UNITED STATES PATENT AND TRADEMARK OFFICE
Certificate

Patent No. 4,551,420                                                      Patented November 5, 1985

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Naohiko Sugimoto, Tetsuro Kojima, and Shingo Ishimaru.

Signed and Sealed this 10th day of June, 1986.

BRADLEY R. GARRIS,
*Office of the Deputy Assistant*
*Commissioner for Patents.*